United States Patent
Schorr et al.

(10) Patent No.: US 6,934,969 B2
(45) Date of Patent: Aug. 30, 2005

(54) ANTI-WICKING PROTECTIVE WORKWEAR AND METHODS OF MAKING AND USING SAME

(75) Inventors: Phillip A. Schorr, Atlanta, GA (US); Michael D. Powers, Canton, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 33 days.

(21) Appl. No.: 10/330,507

(22) Filed: Dec. 27, 2002

(65) Prior Publication Data

US 2004/0123366 A1 Jul. 1, 2004

(51) Int. Cl.[7] ............................................... A41D 13/12
(52) U.S. Cl. ................................................. 2/51; 2/125
(58) Field of Search ............................. 2/59, 60, 455, 2/51, 125, 126, 123, 114, 457, 456, 16, 48, 77, 85, 87, 93, 115, 901, 108, 135; 442/79, 85, 86; 128/846

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| RE28,219 E | 10/1974 | Taylor et al. | |
| 3,849,241 A | 11/1974 | Butin et al. | |
| 3,855,046 A | 12/1974 | Hansen et al. | |
| 3,868,728 A * | 3/1975 | Krzewinski | 2/114 |
| 4,041,203 A | 8/1977 | Brock et al. | |
| 4,171,542 A * | 10/1979 | Cox et al. | 2/51 |
| 4,303,924 A | 12/1981 | Young, Jr. | |
| 4,340,563 A | 7/1982 | Appel et al. | |
| 4,374,888 A | 2/1983 | Bornslaeger | |
| 4,382,262 A | 5/1983 | Savit | |
| 4,389,503 A | 6/1983 | Maxwell et al. | |
| 4,389,734 A * | 6/1983 | Franz et al. | 2/59 |
| 4,478,910 A | 10/1984 | Oshima et al. | |

(Continued)

FOREIGN PATENT DOCUMENTS

| | | |
|---|---|---|
| DE | 2313335 | 1/1975 |
| DE | 2340855 | 6/1975 |
| DE | 2654823 | 6/1978 |
| DE | 2412852 | 5/1979 |
| DE | 19803827 | 8/1999 |
| DE | 19810847 | 9/1999 |
| DE | 19810849 | 5/2000 |
| EP | 0 023 433 A2 | 2/1981 |
| EP | 0 211 524 B1 | 9/1991 |
| EP | 0 304 957 B1 | 4/1994 |
| EP | 0 639 459 A2 | 2/1995 |
| EP | 0 713 774 A2 | 5/1996 |
| EP | 0 471 384 B1 | 10/1996 |

(Continued)

OTHER PUBLICATIONS

RD 173017, Sep. 10, 1978, (abstract).
Pond, Stephen F., "Ink Jet Technology and Product Development Strategies," Published by ©2000 Torrey Pines Research, pp. 198–201, 377–385.
Material Safety Data Sheet; Hot Melt Ink, Cyan, Magenta, Yellow, etc.; pp. 1–3.

(Continued)

*Primary Examiner*—A. Vanatta

(57) ABSTRACT

The present invention relates to protective outerwear or workwear for covering a body portion. The protective outerwear has an inner surface and an outer surface, with the outer surface including thereupon a low surface tension liquid blocking material in a continuous unbroken band for blocking the wicking of at least low surface tension liquid that is contained on the outer surface of the outerwear.

23 Claims, 10 Drawing Sheets

U.S. PATENT DOCUMENTS

| | | | |
|---|---|---|---|
| 4,503,444 A | | 3/1985 | Tacklind |
| 4,504,357 A | | 3/1985 | Holbein et al. |
| 4,504,977 A | * | 3/1985 | King et al. ............... 2/51 |
| 4,526,825 A | | 7/1985 | Whitehead |
| 4,535,481 A | | 8/1985 | Ruth-Larson et al. |
| 4,689,078 A | | 8/1987 | Koike et al. |
| 4,752,972 A | | 6/1988 | Neckerman et al. |
| 4,786,288 A | | 11/1988 | Handa et al. |
| 4,835,208 A | | 5/1989 | Ball |
| 4,841,310 A | | 6/1989 | Hoffman |
| 4,849,770 A | | 7/1989 | Koike et al. |
| 4,909,879 A | | 3/1990 | Ball |
| 4,969,951 A | | 11/1990 | Koike et al. |
| 4,991,232 A | * | 2/1991 | Taylor ...................... 2/51 |
| 5,003,902 A | * | 4/1991 | Benstock et al. ........ 112/418 |
| 5,019,066 A | | 5/1991 | Freeland et al. |
| 5,087,283 A | | 2/1992 | Dixon et al. |
| 5,116,682 A | | 5/1992 | Chakravarti et al. |
| 5,145,727 A | | 9/1992 | Potts et al. |
| 5,151,321 A | | 9/1992 | Reeves et al. |
| 5,169,706 A | | 12/1992 | Collier, IV et al. |
| 5,178,931 A | | 1/1993 | Perkins et al. |
| 5,188,885 A | | 2/1993 | Timmons et al. |
| 5,195,950 A | | 3/1993 | Delannoy |
| 5,213,881 A | | 5/1993 | Timmons et al. |
| 5,214,442 A | | 5/1993 | Roller |
| 5,271,883 A | | 12/1993 | Timmons et al. |
| 5,280,310 A | | 1/1994 | Otsuka et al. |
| 5,371,520 A | | 12/1994 | Kubota |
| 5,444,871 A | * | 8/1995 | Lopez ...................... 2/114 |
| 5,458,590 A | | 10/1995 | Schleinz et al. |
| 5,461,724 A | * | 10/1995 | Wiedner et al. .......... 2/457 |
| 5,464,688 A | | 11/1995 | Timmons et al. |
| 5,466,232 A | | 11/1995 | Cadieux et al. |
| 5,481,281 A | | 1/1996 | Otsuka et al. |
| 5,487,614 A | | 1/1996 | Hale |
| 5,503,076 A | | 4/1996 | Yeo |
| 5,562,037 A | | 10/1996 | Schleinz et al. |
| 5,563,642 A | | 10/1996 | Keefe et al. |
| 5,566,616 A | | 10/1996 | Schleinz et al. |
| 5,571,586 A | | 11/1996 | Gobran |
| 5,586,339 A | | 12/1996 | Lathan |
| 5,591,153 A | | 1/1997 | Mattingly, III |
| 5,594,955 A | | 1/1997 | Sommers |
| 5,597,642 A | | 1/1997 | Schleinz et al. |
| 5,628,067 A | * | 5/1997 | Meyer et al. ............. 2/125 |
| 5,629,063 A | | 5/1997 | Gobran |
| 5,648,805 A | | 7/1997 | Keefe et al. |
| 5,670,004 A | | 9/1997 | Mattingly, III |
| 5,673,433 A | * | 10/1997 | Rothrum ................... 2/46 |
| 5,681,645 A | | 10/1997 | Strack et al. |
| 5,694,739 A | | 12/1997 | Mattingly, III |
| 5,695,855 A | | 12/1997 | Yeo et al. |
| 5,695,868 A | | 12/1997 | McCormack |
| 5,705,251 A | | 1/1998 | Morman et al. |
| 5,720,738 A | | 2/1998 | Clark |
| 5,755,906 A | | 5/1998 | Achter et al. |
| 5,759,673 A | | 6/1998 | Ikezawa et al. |
| 5,762,642 A | | 6/1998 | Coles et al. |
| 5,769,837 A | | 6/1998 | Parr |
| H1746 H | | 8/1998 | Carrier et al. |
| 5,797,894 A | | 8/1998 | Cadieux et al. |
| 5,807,365 A | | 9/1998 | Luceri |
| 5,843,254 A | | 12/1998 | Clark |
| 5,851,274 A | | 12/1998 | Lin |
| 5,851,595 A | | 12/1998 | Jones, Jr. |
| 5,853,859 A | | 12/1998 | Levy et al. |
| 5,855,999 A | | 1/1999 | McCormack |
| 5,895,505 A | | 4/1999 | Yamamoto et al. |
| 5,919,539 A | | 7/1999 | Bisbis et al. |
| 5,931,824 A | | 8/1999 | Stewart et al. |
| 5,972,082 A | | 10/1999 | Koyano et al. |
| 5,985,396 A | | 11/1999 | Kerins et al. |
| 6,013,347 A | | 1/2000 | Martin et al. |
| 6,020,405 A | | 2/2000 | Matzinger et al. |
| 6,024,220 A | | 2/2000 | Smith et al. |
| 6,037,281 A | | 3/2000 | Mathis et al. |
| 6,050,666 A | | 4/2000 | Yeoh et al. |
| 6,051,036 A | | 4/2000 | Kusaki et al. |
| 6,096,412 A | | 8/2000 | McFarland et al. |
| 6,103,364 A | | 8/2000 | Harris et al. |
| 6,106,922 A | | 8/2000 | Cejka et al. |
| 6,120,888 A | | 9/2000 | Dolsey et al. |
| 6,132,858 A | | 10/2000 | Kloos |
| 6,141,799 A | | 11/2000 | Morris |
| 6,142,984 A | | 11/2000 | Brown et al. |
| 6,146,770 A | | 11/2000 | Sargeant et al. |
| 6,149,259 A | | 11/2000 | Otsuka et al. |
| 6,150,005 A | | 11/2000 | Williams et al. |
| 6,159,581 A | | 12/2000 | Yoneda et al. |
| 6,183,587 B1 | | 2/2001 | McFall et al. |
| 6,199,968 B1 | | 3/2001 | Katakura et al. |
| 6,231,652 B1 | | 5/2001 | Koyano et al. |
| 6,235,098 B1 | | 5/2001 | Maekawa et al. |
| 6,235,659 B1 | | 5/2001 | McAmish et al. |
| 6,245,410 B1 | | 6/2001 | Hahnle et al. |
| 6,254,582 B1 | | 7/2001 | O'Donnell et al. |
| 6,258,427 B1 | | 7/2001 | Kerins et al. |
| 6,263,816 B1 | | 7/2001 | Codos et al. |
| 6,265,053 B1 | | 7/2001 | Kronzer et al. |
| 6,266,436 B1 | | 7/2001 | Bett et al. |
| H1978 H | | 8/2001 | Freiburger et al. |
| 6,286,144 B1 | * | 9/2001 | Henderson et al. ........... 2/69 |
| 6,316,688 B1 | | 11/2001 | Hammons et al. |
| 6,395,957 B1 | | 5/2002 | Chen et al. |
| 6,530,090 B1 | * | 3/2003 | Ambrose et al. ............ 2/59 |
| 6,851,125 B2 | * | 2/2005 | Fujikawa et al. ........... 2/51 |
| 2002/0007834 A1 | | 1/2002 | Trotter et al. |
| 2003/0079272 A1 | * | 5/2003 | Poppe ...................... 2/114 |

FOREIGN PATENT DOCUMENTS

| | | |
|---|---|---|
| EP | 0 747 029 A1 | 12/1996 |
| EP | 0 805 027 A2 | 11/1997 |
| EP | 0 604 729 B1 | 3/1998 |
| EP | 0 809 680 B1 | 12/1998 |
| EP | 1 059 340 A1 | 12/2000 |
| EP | 1 070 596 A2 | 1/2001 |
| EP | 1 164 007 A1 | 12/2001 |
| EP | 1 186 431 A2 | 3/2002 |
| EP | 0 861 154 B1 | 4/2002 |
| EP | 1 062 095 B1 | 6/2002 |
| EP | 1224876 A2 | 7/2002 |
| EP | 0 764 550 B1 | 11/2002 |
| FR | 2741296 | 5/1997 |
| GB | 2 128 439 | 4/1984 |
| GB | 2 334 684 | 9/1999 |
| JP | 55-051 583 A2 | 4/1980 |
| JP | 57-115 352 A2 | 7/1982 |
| JP | 60-104 076 A2 | 6/1985 |
| JP | 85-027 588 B | 6/1985 |
| JP | 60-169 489 A2 | 9/1985 |
| JP | 60-245 557 A2 | 12/1985 |
| JP | 61-118 473 A2 | 6/1986 |
| JP | 61-179 269 A2 | 8/1986 |
| JP | 61-179 271 A2 | 8/1986 |
| JP | 61-179 272 A2 | 8/1986 |
| JP | 61-179 273 A2 | 8/1986 |
| JP | 63-265 680 A2 | 11/1988 |
| JP | 01-013 518 A2 | 1/1989 |
| JP | 03-104 646 A2 | 5/1991 |
| JP | 03-049 311 B4 | 7/1991 |

| | | |
|---|---|---|
| JP | 92-015 746 B | 3/1992 |
| JP | 04-251 747 A | 9/1992 |
| JP | 04-292 947 A2 | 10/1992 |
| JP | 05-035 191 B4 | 5/1993 |
| JP | 05-230 409 A2 | 9/1993 |
| JP | 05-247 390 A2 | 9/1993 |
| JP | 05-331 396 A2 | 12/1993 |
| JP | 06-127 032 A2 | 5/1994 |
| JP | 06-246 934 A2 | 9/1994 |
| JP | 06-286 134 A2 | 10/1994 |
| JP | 06-312 509 A2 | 11/1994 |
| JP | 07-034 019 A2 | 2/1995 |
| JP | 07-068 922 A2 | 3/1995 |
| JP | 07-089 077 A2 | 4/1995 |
| JP | 07-125 197 A2 | 5/1995 |
| JP | 07-156 407 A2 | 6/1995 |
| JP | 07-213 310 A | 8/1995 |
| JP | 07-241 983 A2 | 9/1995 |
| JP | 07-304 167 A2 | 11/1995 |
| JP | 07-314 694 A2 | 12/1995 |
| JP | 07-314 728 A2 | 12/1995 |
| JP | 07-323 657 A2 | 12/1995 |
| JP | 08-052 903 A2 | 2/1996 |
| JP | 08-118 617 A2 | 5/1996 |
| JP | 08-164 602 A2 | 6/1996 |
| JP | 08-174 995 A2 | 7/1996 |
| JP | 08-187 933 A2 | 7/1996 |
| JP | 08-216 395 A2 | 8/1996 |
| JP | 08-259 868 A2 | 10/1996 |
| JP | 08-267 733 A2 | 10/1996 |
| JP | 08-309 987 A2 | 11/1996 |
| JP | 09-031 866 A2 | 2/1997 |
| JP | 09-039 233 A2 | 2/1997 |
| JP | 2 593 830 B2 | 3/1997 |
| JP | 09-057 966 A2 | 3/1997 |
| JP | 09-066 661 A2 | 3/1997 |
| JP | 2 618 359 B2 | 6/1997 |
| JP | 09-175 004 A2 | 7/1997 |
| JP | 09-175 005 A2 | 7/1997 |
| JP | 09-175 006 A2 | 7/1997 |
| JP | 09-175 007 A2 | 7/1997 |
| JP | 09-194 781 A2 | 7/1997 |
| JP | 09-226 229 A2 | 9/1997 |
| JP | 09-240 138 A2 | 9/1997 |
| JP | 09-268 482 A2 | 10/1997 |
| JP | 09-268 484 A | 10/1997 |
| JP | 09-286 102 A2 | 11/1997 |
| JP | 09-314 984 A2 | 12/1997 |
| JP | 10-034 967 A2 | 2/1998 |
| JP | 10-044 408 A2 | 2/1998 |
| JP | 2 732 999 B2 | 3/1998 |
| JP | 2 758 788 B2 | 5/1998 |
| JP | 10-138 504 A2 | 5/1998 |
| JP | 10-138 510 A2 | 5/1998 |
| JP | 10-138 516 A2 | 5/1998 |
| JP | 10-138 520 A2 | 5/1998 |
| JP | 10-138 521 A2 | 5/1998 |
| JP | 10-193 610 A2 | 7/1998 |
| JP | 10-264 498 A2 | 10/1998 |
| JP | 10-278 312 A2 | 10/1998 |
| JP | 11-010-852 A2 | 1/1999 |
| JP | 11-010 853 A2 | 1/1999 |
| JP | 11-061 021 A2 | 3/1999 |
| JP | 11-099 646 A2 | 4/1999 |
| JP | 11-188 968 A2 | 7/1999 |
| JP | 11-207 951 A2 | 8/1999 |
| JP | 11-268 284 A2 | 10/1999 |
| JP | 11-268 405 A2 | 10/1999 |
| JP | 11-277 772 A2 | 10/1999 |
| JP | 2000-000 266 A | 1/2000 |
| JP | 2000-043 401 A2 | 2/2000 |
| JP | 2000-052 640 A2 | 2/2000 |
| JP | 2000-127 611 A2 | 5/2000 |
| JP | 2000-190 628 A2 | 7/2000 |
| JP | 2000-203 150 A2 | 7/2000 |
| JP | 2000-233 571 A2 | 8/2000 |
| JP | 3 089 308 B2 | 9/2000 |
| JP | 3 089 583 B2 | 9/2000 |
| JP | 2000-238 410 A2 | 9/2000 |
| JP | 2000-256 974 A2 | 9/2000 |
| JP | 2000-296 670 A | 10/2000 |
| JP | 2001-010 031 A2 | 1/2001 |
| JP | 2001 018 518 A2 | 1/2001 |
| JP | 2001 020 185 A2 | 1/2001 |
| JP | 2001 039 017 A2 | 2/2001 |
| NL | 9400024 A | 8/1995 |
| WO | WO 95/02973 | 2/1995 |
| WO | WO 95/15410 | 6/1995 |
| WO | WO 96/31345 | 10/1996 |
| WO | WO 97/18090 | 5/1997 |
| WO | WO 98/43821 | 10/1998 |
| WO | WO 99/33669 | 7/1999 |
| WO | WO 99/43760 | 9/1999 |
| WO | WO 99/55269 | 11/1999 |
| WO | WO 99/55270 | 11/1999 |
| WO | WO 99/55271 | 11/1999 |
| WO | WO 99/60973 | 12/1999 |
| WO | WO 99/65700 | 12/1999 |
| WO | WO 00/07426 | 2/2000 |
| WO | WO 00/35401 | 6/2000 |
| WO | WO 00/40195 | 7/2000 |
| WO | WO 00/40196 | 7/2000 |
| WO | WO 00/42960 | 7/2000 |
| WO | WO 00/56972 | 9/2000 |
| WO | WO 00/69950 | 11/2000 |
| WO | WO 00/72984 | 12/2000 |
| WO | WO 00/73063 | 12/2000 |
| WO | WO 00/76441 | 12/2000 |
| WO | WO 01/02254 | 1/2001 |
| WO | WO 01/03529 | 1/2001 |
| WO | WO 01/27382 | 4/2001 |
| WO | WO 01/31122 | 5/2001 |
| WO | WO 01/31124 | 5/2001 |
| WO | WO 01/32318 | 5/2001 |
| WO | WO 01/36171 | 5/2001 |
| WO | WO 01/36209 | 5/2001 |
| WO | WO 01/49230 | 7/2001 |
| WO | WO 01/50412 | 7/2001 |
| WO | WO 02/14080 | 2/2002 |
| WO | WO 02/051644 | 7/2002 |

OTHER PUBLICATIONS

Material Safety Data Sheet; Hot Melt Ink, Black, High; JET 7520/JET 7533; pp. 1–4.

Sales Literature; Oct. 1, 2002; Spectra Inc.; "Galaxy PH 256/80 HM".

Hydrophobic Surfaces, edited by F. M. Fowkes of the Academic Press, New York, 1969, pp. 1–27.

Shaw, Duncan J., "Introduction to Colloid and Surface Chemistry", Third Edition, Butterworths 1980, pp. 131–135.

Pocket Guide to Color Reproduction, Communication and Control, by Miles Southworth (1972), pp. 1–7.

American Society for Testing and Materials (ASTM) Designation: F1571–95, "Standard Test Method for Determination of Abrasion and Smudge Resistance of Images Produced from Business Copy Products", Nov. 1995, pp. 1409–1412.

AATCC Evaluation Procedure 8, "AATCC 9–Step Chromatic Transference Scale", AATCC Technical Manual, 1999, pp. 378–379.

* cited by examiner

ANTI-WICKING PROTECTIVE WORKWEAR AND METHODS OF MAKING AND USING SAME

BACKGROUND OF THE INVENTION

The present invention pertains to protective workwear. More specifically, the present invention pertains to surgical gowns and other protective workwear that offer additional contamination protection to users of such workwear, and methods of making and using the same.

With the burgeoning costs of medical care, and the sterilization costs associated with cleansing medical supplies that may have been exposed to blood born pathogens and other contaminants, manufacturers of medical supplies such as medical equipment and protective medical apparel have sought to reduce costs of such supplies to medical service providers. In this regard, medical supply manufacturers have turned to the production of disposable medical supplies so as to reduce the time and labor costs associated with sterilization, and to provide enhanced options to medical service providers for products that need not be reused. For the purposes of this application, the term "medical service provider" is meant to encompass all persons who treat either human or animal patients through the course of their employment or otherwise, or are exposed to blood or other types of low surface tension liquids containing contaminants, during the course of their employment or otherwise.

Further, with the onset of the autoimmune deficiency syndrome (HIV virus) and other blood born pathogens, such as hepatitis, there has been a concentrated effort to provide medical service providers with barrier protection to such viruses. To this end, protective workwear used in medical procedures, i.e., medical garments, such as hospital and surgical gowns, have been made from nonwoven materials instead of traditional woven materials, such as cotton and linen-based fabrics.

In particular, cloth-like multi-layered fibrous nonwoven laminates, films or film laminates, and film and fibrous nonwoven laminate composites, have been produced that offer barrier protection when employed as medical garment material. Such materials have proven in some circumstances, to be liquid-impervious, but breathable. For instance, if such garment materials are made from only fibrous nonwoven materials and/or breathable films, such materials have allowed the passage of gasses in order to provide the necessary thermal comfort to medical service providers, but without sacrificing high levels of protection. If such garments are made from monolithic films or film composites, such garments are often uncomfortable to wear as they restrict the ability of air to easily pass through them. If such garments are made of fibrous material, but are additionally coated with certain film-like coatings to provide a moisture barrier, such materials are likewise uncomfortable to wear. For instance, it is known to coat large portions of hospital or surgeon's garments in the arm and abdominal areas. While such garments may provide large barriers to liquids that may be present in a hospital setting, such garments are often uncomfortable since they fail to breathe in these same large protected areas. Further, if large areas of such garments are coated with a liquid barrier, such film coating may fail to provide the necessary coefficient of friction which is required for the sustained placement of a glove over such materials, as is the practice in a hospital or operating room in which gloves are placed over the sleeves of a surgeon or other medical service provider. Since such liquid repellant coatings are often expensive, such coatings may also add a significant expense to the costs of such garments. Finally, despite these additional coatings, medical personnel often use multiple layers of such nonwoven garments in order to create enhanced barrier protection (that is, they wear several gowns, one over the other). While such a practice may provide the desired barrier protection, such protection is almost always accompanied with a sacrifice in thermal comfort. Therefore, even with improvements in the disposable protective outerwear field, there continues to be a need for apparel with increased barrier protection, without a sacrifice in comfort.

Furthermore, despite the aforementioned improvements in materials, there continues to be breaches of the barriers while they are being used by medical service providers. The breaches can occur for many different reasons, such as a medical garment being caught on a medical instrument or device during a medical procedure, thereby creating a gap between pieces of clothing, or a medical garment actually being pierced during a medical procedure, or because liquid present in a medical setting may wick along a nonwoven material surface, or alternatively in conjunction with a glove line (that is, the inside surface of a glove in contact with a nonwoven material surface) to a location on the medical service provider where there is either no or reduced barrier protection. For instance, as can be seen in FIG. 1, if a medical practitioner is exposed to large amounts of blood during a medical procedure, it is possible for blood to wick along a glove or booty (foot cover for foot protection) line as the case may be, that is adjacent and overlapping a nonwoven garment sleeve or leg, and eventually to the inside surface of the glove or shoe cover. For the purposes of this application, the term "outer surface" shall mean the surface of protective workwear facing away from a person wearing such workwear. The term "inner surface" shall mean the surface of protective workwear facing the body of the person wearing the protective workwear, i.e. facing the skin of the person. Protective workwear may have one or more layers which provide an outer surface, and one or more layers which provide an inner surface.

As can be seen in FIG. 1, a porcelain model arm 10 of a medical service provider's hand has been donned with one surgical glove 20 (easily seen by the rolled up glove edge ridge or "beaded" edge). Prior to the donning of the glove 20, an exemplary sleeve 25 of a medical gown or garment 30 has been placed over the model's wrist, and lower arm area, with the sleeve 25 including a cuff 32. The glove 20 has then been placed over the model, and in an overlapping fashion, over the cuffed lower sleeve portion of the garment 30 Liquid 34 (in this case, 20% isopropyl alcohol and water with red food coloring for ease of visualization, (all with surface tension of approximately 32 dynes/cm, as a preliminary model for blood having a surface tension of approximately 40 dynes/cm)) is shown to have wicked along the outer surface 35 of the nonwoven garment, along the inner surface (not shown) of the glove and up the inner surface of the nonwoven garment. Subsequently, the arm 10 became wet at various locations.

Of course, whether such liquid actually reaches the hand/limb of a medical service provider does depend on a number of factors, such as the practice of a medical service provider to double glove (or double donning), that is, the practice of medical providers to place two or more gloves or other coverings over their hands/limbs. The order of double gloving is also significant. That is, one glove is placed under a medical garment and one glove is placed over a medical garment. Alternatively, two gloves are placed one on top of the other, each over the garment. Other variables include the types of gloves utilized (for instance, the size of the wrist/arm portion, and the composition of the glove) and the tension that they apply to the arm of the user. Additional variables include the liquid that is exposed to the medical service provider, the garment utilized (for instance whether the garment has sleeves and how long such sleeves are, and the composition of the medical garment), the number of garments worn by the medical service provider (for example, two sleeves from two garments worn over the arm) and of course the medical service provider's safety practices in dealing with large volumes of blood and other liquids containing potential contaminants.

Therefore, there is a need for medical and other protective workwear/outerwear apparel which may assist in reducing the possibility of wicking of blood and other liquids along an apparel surface and/or along the inside surface of protective gloves/boots/or other workwear that may be used in conjunction with the protective workwear.

SUMMARY OF THE INVENTION

A protective workwear for covering a body portion is provided which has an inner surface and an outer surface. The outer surface includes a low surface tension liquid blocking material in a continuous unbroken band for blocking the wicking of at least low surface tension liquid that is contained on the outer surface of said outerwear.

DEFINITIONS

Figure 1:
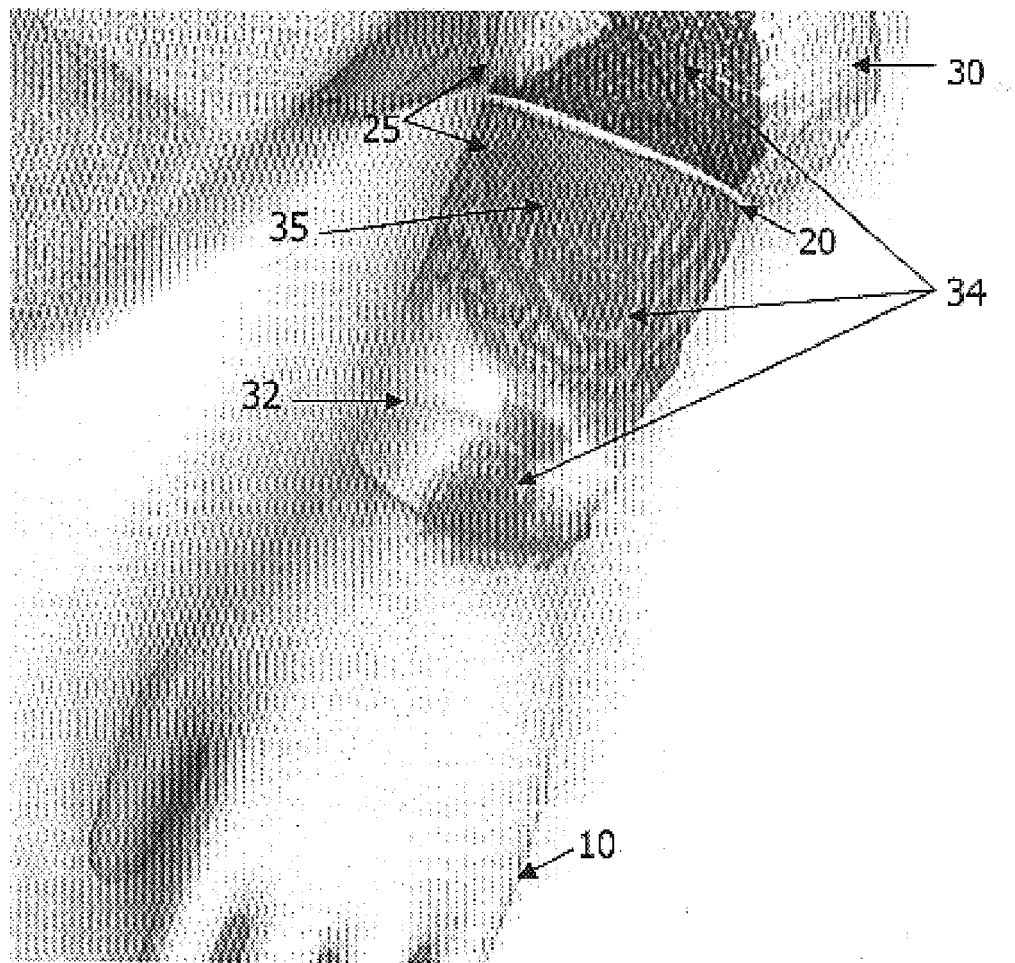
FIG. 1 illustrates a photographic image of a prior art nonwoven fabric sleeve over a hand model and including a glove positioned over the model and sleeve edge.

As used herein the following terms have the specified meanings, unless the context demands a different meaning, or a different meaning is expressed; also, the singular generally includes the plural, and the plural generally includes the singular unless otherwise indicated.

As used herein, the terms "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof.

As used herein, the term "fabric" refers to all woven, knitted and nonwoven fibrous webs, unless one type is specified.

As used herein, the term "layer" when used in the singular can have the dual meaning of a single element or a plurality of elements.

As used herein the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. which is incorporated by reference herein in its entirety. Meltblown fibers are microfibers which may be continuous or discontinuous, are generally smaller than 10 microns in average diameter, and are generally tacky when deposited onto a collecting surface.

As used herein "multi-layer laminate" means a laminate wherein some of the layers are spunbond and some meltblown such as a spunbond/meltblown/spunbond (SMS) laminate and others as disclosed in U.S. Pat. No. 4,041,203 to Brock et al., U.S. Pat. No. 5,169,706 to Collier, et al., U.S. Pat. No. 5,145,727 to Potts et al., U.S. Pat. No. 5,178,931 to Perkins et al. and U.S. Pat. No. 5,188,885 to Timmons et al. each of which are incorporated by reference herein in their entirety. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 to 12 osy (6 to 400 gsm), or more particularly from about 0.75 to about 3 osy. Multi-layer laminates may also have various numbers of meltblown (M) layers or multiple spunbond (S) layers in many different configurations and may include other materials like films (F) or coform materials, e.g. SMMS, SM, SFS, SMS etc.

As used herein the terms "bonded" and "bonding" refer to the joining, adhering, connecting, attaching, or the like of two elements. Two elements will be considered to be bonded together when they are bonded directly to one another or indirectly to one another, such as when each is directly bonded to intermediate elements. Such bonding may occur for example, by adhesive, thermal or ultrasonic methods.

As used herein the term "thermal point bonding" or "thermal bonding" involves passing a fabric or web of fibers to be bonded between a heated calender roll and an anvil roll. When layers of fabric, or two or more fabrics, are thermally bonded, the fabric(s) is/are respectively, heated to a melting point, such that all pores, capillaries, and so forth, if any, in the material collapse and/or are sealed in the melting process. The integrity and continuity of the material is maintained (i.e., the material does not become too thin or perforated in the bonded areas).

The calender roll is usually, though not always, patterned in some way so that the entire fabric is not bonded across its entire surface (thermal point bonding), and the anvil roll is usually flat. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings, incorporated herein by reference in its entirety. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds with about a 16% bond area and a wire weave pattern looking as the name suggests, e.g. like a window screen, with about a 19% bond area. Typically, the percent bonding area varies from around 10% to around 30% of the area of the fabric laminate web. As is well known in the art, the spot bonding holds the laminate layers together as well as imparts integrity to each individual layer by bonding filaments and/or fibers within each layer.

As used herein, the term "ultrasonic bonding" or "ultrasonic welding" means a process performed, for example, by passing a fabric, such as a nonwoven material, between a sonic horn and anvil roll as illustrated in U.S. Pat. No. 4,374,888 to Bornslaeger, incorporated by reference herein in its entirety. When layers of fabric, or two or more fabrics, are ultrasonically bonded, the fabric(s) is/are respectively, heated to a melting point, such that all pores, capillaries, and so forth, if any, in the material collapse and/or are sealed in the melting process. The integrity and continuity of the material is maintained (i.e., the material does not become too thin or perforated in the bonded areas).

As used herein, the terms "nonwoven" and "nonwoven fabric" mean either a nonwoven web, a film, a foam sheet material, or a combination thereof.

As used herein the terms "fibrous nonwoven" and "fibrous nonwoven fabric or web" mean a web having a structure of individual fibers, filaments or threads which are interlaid, but not in an identifiable manner as in a knitted fabric. Fibrous nonwoven fabrics or webs have been formed from many processes such as for example, meltblowing processes, spunbonding processes, and bonded carded web processes. The basis weight of fibrous nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein, the term "protective workwear" shall encompass medical garments or medical workwear and other forms of protective attire used by various industries/professions to protect workers from contaminants or to prevent the contamination of others. Such protective workwear includes but is not limited to hospital and surgical gowns, medical scrubs, medical drapes, coveralls, and garments used to protect either a portion of, or an entire body. For the purposes of this application, the terms "garment(s)" and "apparel" are used synonymously.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. each of which are incorporated by reference herein in their entirety. Spunbond fibers are generally not tacky when they are deposited onto a collecting surface. Spunbond fibers are generally continuous and often have average diameters (from a sample of at least 10) larger than 7 microns, more particularly, between about 10 and 20 microns.

The term "low surface tension liquid" shall mean liquids that demonstrates a surface tension of between about between about 25 and 50 dynes/cm, but typically between about 30 and 45 dynes per cm. Surface tension may be measured in accordance with standard Wilhemy plate or tensiometer methods. Such low surface tension liquids include, but are not limited to scrub solutions, blood, isopropyl alcohol and other liquids that are commonly encountered during a medical procedure or in a medical environment.

The related term "hydrophobic" shall generally refer a nonwoven fabric that does not promote the spreading of water. The water instead, forms drops and a contact angle that can be measured from the plane of the fiber/material surface, tangent to the water surface at the three-phase boundary line (air-water-fiber). Typically the contact angle ranges from 40–110 degrees, and is often greater than 90 degrees. The fiber/material also demonstrates a surface tension or energy of less than about 50 dynes/cm, such as between about 10–50 dynes/cm. Further elaboration on hydrophobic materials may be found in Hydrophobic Surfaces, edited by F. M. Fowkes of the Academic Press, New York, 1969, page 1. Hydrophobic fabrics may be produced from materials that are inherently hydrophobic or from hydrophilic fibers/films that have been treated in some fashion to be hydrophobic. Such treatment may include chemical treatments.

Contact angles can be measured by standard measurement techniques such as those described in the Introduction to Colloid and Surface Chemistry by Duncan J. Shaw, Third Edition, Butterworths 1980, pages 131–135, incorporated herein by reference. Surface energy of materials can be measured using dyne pen sets, such as those available from UV Process Supply, Inc., of Chicago, Ill. However, additional methods of measuring surface energy include Torsion Balance apparatus and other devices, which utilize platinum rings, such as those available from Torsion Balance Supplies of the United Kingdom.

The term "low surface tension liquid blocking material" shall mean a treatment which results in material that will block the travel path of wicking low surface tension liquid. Such term shall include but not be limited to thermal bonding or welding and ultrasonic bonding or welding. It is used interchangeably with the term "circumambient material".

The term "colored" or "coloring" shall mean containing a colorant or coloring agent which is visually perceptible to the human eye. For the purpose of this application, such colorant may include pigments, dyes, and so forth.

The term "wick" or "wicking" shall mean to carry moisture/liquid away, typically by capillary action. Such term also encompasses the ability of a liquid to travel between sheet materials, such as between the surface of a fibrous nonwoven sheet material such as a surgical drape and a film sheet, such as a glove.

The term "contaminant" shall mean a chemical agent or biological organism/pathogen that can potentially harm a human being or animal.

These terms may be defined with additional language in the remaining portions of the specification.

DETAILED DESCRIPTION OF THE INVENTION

A structure has been developed to reduce the likelihood that low surface tension liquid such as blood will wick along the surface of a nonwoven material, and further, to reduce the likelihood that low surface tension liquids will wick between the surface of nonwoven materials of protective workwear such as medical garments and the inside surface of gloves worn over such workwear, so as to avoid the liquid traveling around or past the edges of such workwear to exposed areas of human skin. For example, such a structure will reduce the likelihood that blood will wick along the surface of surgical gowns and along the inside surface of gloves or foot coverings worn over such gowns.

Such a structure includes a nonwoven medical garment that has been treated to include a continuous line or band of low surface tension liquid blocking material which significantly reduces or blocks a low surface tension liquid at least along an outer surface portion of a sleeve, leg, waist, or neck opening of such garment. Such low surface tension liquid blocking material is desirably situated adjacent the opening of such a garment. In the case of a sleeve, such low surface tension liquid blocking material is desirably at a location on a sleeve over which a glove will be placed during usage. For a leg, such low surface tension liquid blocking material is desirably at a location on a pant leg over which a booty or shoe cover will be placed during usage. For a shirt garment, such low surface tension liquid blocking material is desirably placed adjacent the waist portion, desirably above that portion of the garment that would be tucked in such that the continuous low surface tension liquid blocking material would not be gathered so as to break the continuity of the line or create overlapping of the fabric. For pants, the low surface tension liquid blocking material should desirably be below the gathered waist portion. If such low surface tension liquid blocking material would be gathered or overlapped it is possible that the continuous line of circumambient material would be broken. In this fashion, such low surface tension liquid blocking material desirably acts as a dam or gutter to prevent such low surface tension liquid from approaching the edges of a garment that surround a wearer's body part.

The low surface tension liquid blocking material is created by thermal bonding or ultrasonic bonding of the garment to provide a continuous low surface tension liquid blocking material which significantly reduces and/or blocks the wicking of low surface tension liquid along at least an outer surface portion of a sleeve, leg, waist, or neck portion of such a garment. Such a low surface tension liquid blocking material can be described generally as a sufficiently wide and continuous area of thermal bonding or ultrasonic bonding to seal the material and to provide a continuous line of material that blocks wicking, especially wicking of low surface tension liquid. Such a low surface tension liquid blocking material does not include the portion of a garment that encompasses an entire arm, leg, neck or waist area, as such would potentially interfere with the comfort of the garment containing the treatment, and would unnecessarily add to the cost of such garments. As used herein, the terms "treated" and "treatment" includes thermal bonding and/or ultrasonic bonding of a garment in an area or region, in continuous linear and/or non-linear lines, paths, bands, and so forth, which sufficiently melts, seals and/or blocks pores, if any, of the garment in the treated area or region, desirably through the entire thickness and/or layers of the garment. Desirably, such treated region, namely, the low surface tension liquid blocking material on the garment or workwear is immediately adjacent an untreated area, so as to provide contact areas of varying coefficients of friction, should a glove or shoe cover be placed over such workwear areas. In this fashion, the glove or shoe cover is less likely to slide during use, as the varying coefficients of friction provide degrees of traction to maintain the glove/shoe cover or other covering in position. Further, since the continuous low surface tension liquid blocking material(s) significantly reduce or block wicking of low surface tension liquid, areas of blocking material acts as a gutter, holding the liquid above the line of blocking material, thereby redirecting the liquid. Untreated areas adjacent the blocking material(s) offer both varying coefficients of friction and, in some instances, some levels of surface absorption (in a garment with at least one inner barrier layer), and serve to hold the low surface tension liquid within a defined outer layer of the garment and in an area adjacent the low surface tension liquid blocking material.

In the case of a medical garment, such as a hospital or surgical gown, which desirably includes a body covering portion with sleeves extending from the body portion that ends in cuffs, such low surface tension liquid blocking material is desirably situated on a sleeve covering each arm, between the cuff region (adjacent a wrist and/or hand) and the elbow region of a gown. Such low surface tension liquid blocking material is desirably equidistant from the cuff edge of the sleeve or leg of the protective medical garment or workwear (that is, the edge of the garment opening surround the limb), but is not required to be so situated.

Figure 5A:
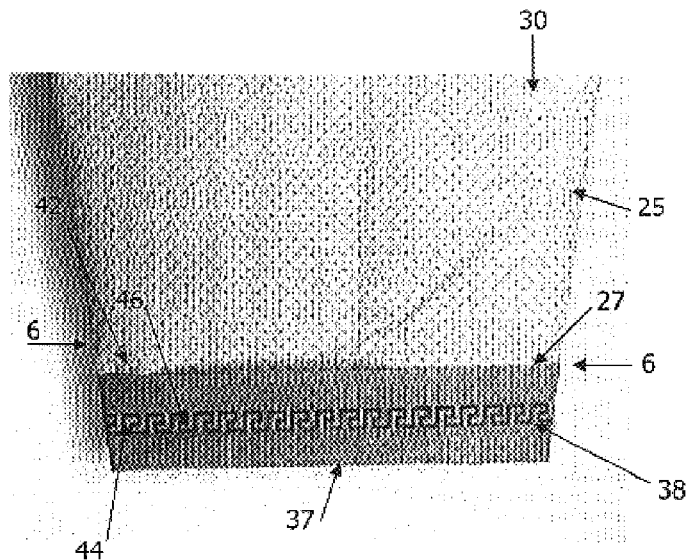
FIGS. 5A–5C illustrate a photographic image of an alternate embodiment of a nonwoven sleeve in constructed in accordance with the present invention in which a lower end of the sleeve has been turned upward, and in which a plurality of continuous ultrasonic bonded bands, the bands having a pattern, are positioned circumferentially about a sleeve surface.
Figure 5B:
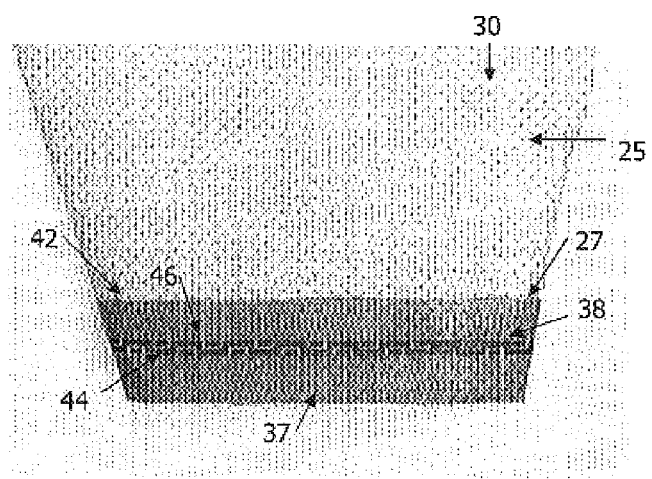
Figure 5C:
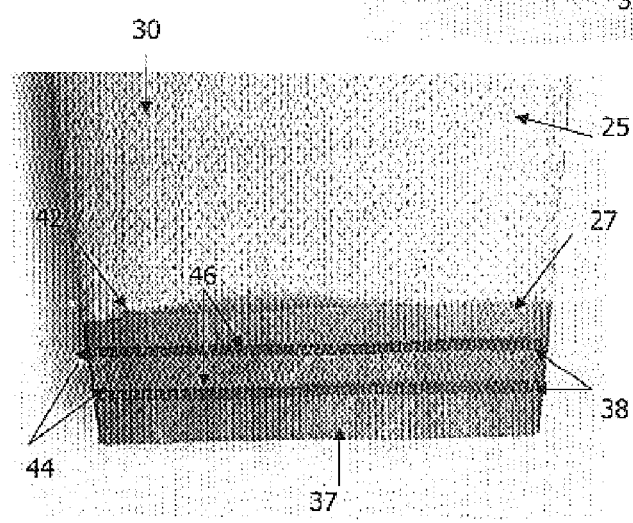

While such low surface tension liquid blocking material may be formed in a continuous straight line around the garment, it is not necessary that such be the case. For instance, such low surface tension liquid blocking material may be provided in any regular and/or irregular pattern around the circumference of the garment or portion thereof, so long as it is continuous, without any breaks or gaps. For example, a continuous artistic pattern, as illustrated in FIGS. 5A–5C, may be employed in order to make the garment more aesthetically pleasing.

In the case of protective medical garments or workwear, such low surface tension liquid blocking material desirably is positioned at a location on a sleeve that will be covered by a glove, when a glove is positioned over such sleeve during the medical service provider's preparatory dressing. By allowing the low surface tension liquid blocking material to be present only in the forms of relatively narrow bands or regions, a gown treated in such a fashion, provides a gutter under the glove to substantially reduce and/or block the spread of wicking liquid, and also provides for the frictional contact of the gown sleeve and a glove, thereby allowing the glove to remain securely positioned over the gown. Further, such strategic placement of low surface tension liquid blocking material is cost efficient, thereby leading to lower cost garments.

Figure 2:
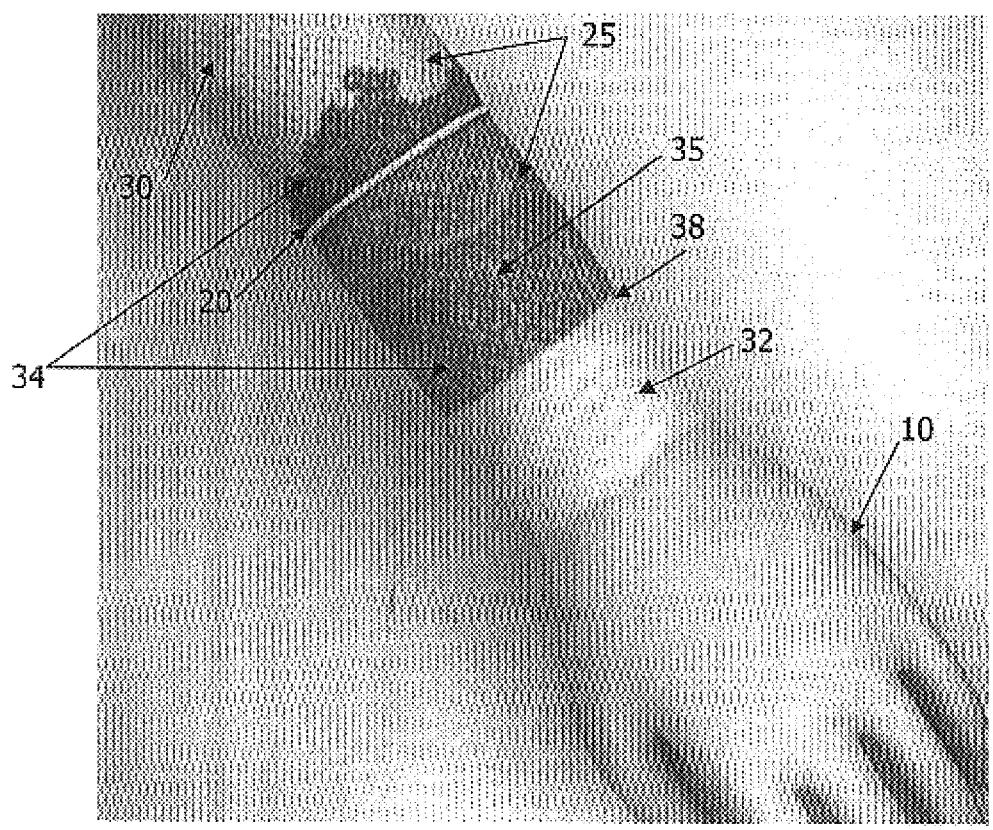
FIG. 2 illustrates a photographic image of a nonwoven fabric sleeve constructed in accordance with the present invention, positioned over a hand model and including a glove positioned over the model and sleeve edge.

Referring now in detail to the drawing figures, wherein like reference numerals represent like parts throughout the several views, one embodiment can be seen in FIG. 2, which illustrates a photographic image of a nonwoven fabric sleeve 25 having a treated cuff 32 in accordance with the invention. In the photograph, a model hand 10 includes a glove 20 positioned over the model hand 10 and sleeve 25. A discrete line of demarcation which is a continuous band of low surface tension liquid blocking material 38 is evident on the sleeve 25 which separates a portion of a sleeve 25 that has been exposed to a low surface tension liquid 34, and a portion of a sleeve 25 which has not. The treated nonwoven medical garment 30 has a continuous low surface tension liquid blocking material 38 on the garment 30 in the configuration of a narrow band, which effectively prevents the wicking of liquid 34 beyond the blocking material 38 along the outer surface 35 of the sleeve 25 and under the glove 20. As a result, liquid does not wick up the inner layer of the nonwoven garment 30 (the inner surface or layer of the garment in contact with the medical service provider's arm). Subsequently, the model arm 10 remains dry. Additionally, the low surface tension liquid 34 is maintained on the outer surface 35 of the garment 30.

Figure 3:
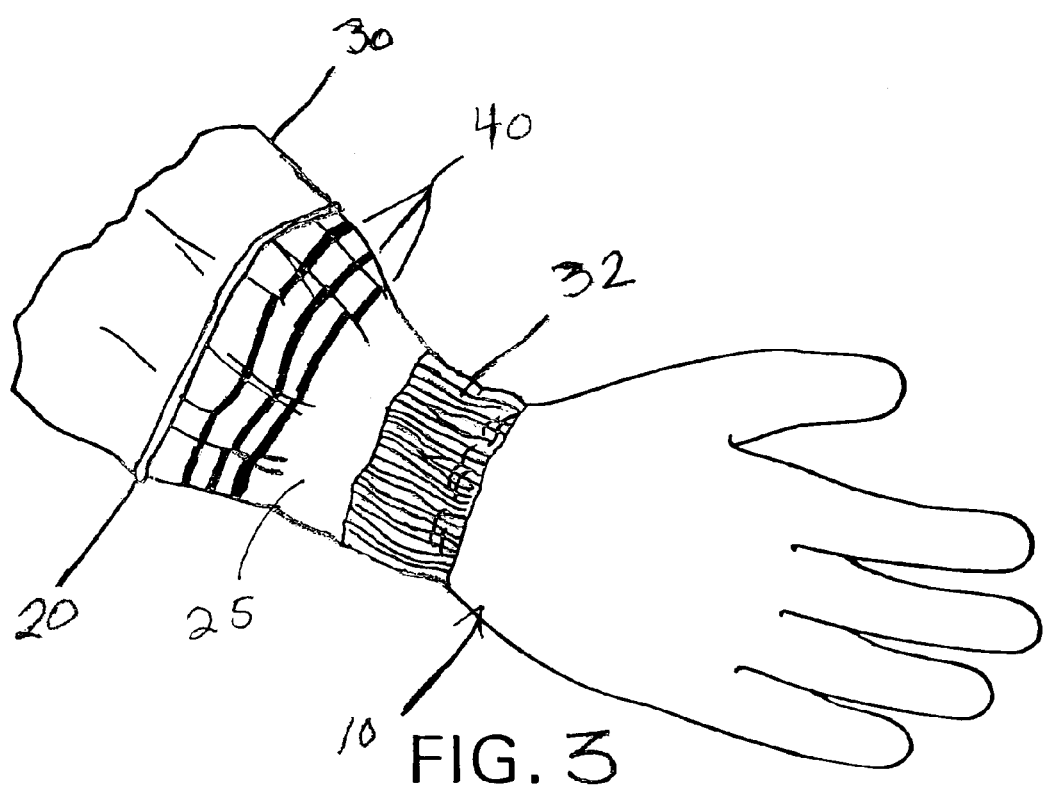
FIG. 3 illustrates a perspective view of an alternate embodiment of a nonwoven sleeve constructed in accordance with the invention which includes a plurality of continuous ultrasonic bonded bands positioned circumferentially about a sleeve surface.

In FIG. 3, an alternate embodiment of the treated garment shown in FIG. 2 is illustrated. In this embodiment, a plurality of low surface tension liquid blocking materials in the form of a plurality of bands 40 surround the garment sleeve 25, thereby creating a multiple stepped barrier to low surface tension liquids. An untreated area on the garment 30 is situated between each of the bands 40. While the bands 40 are shown as seen through the glove 20, it is not necessary that they be so.

Figure 4:
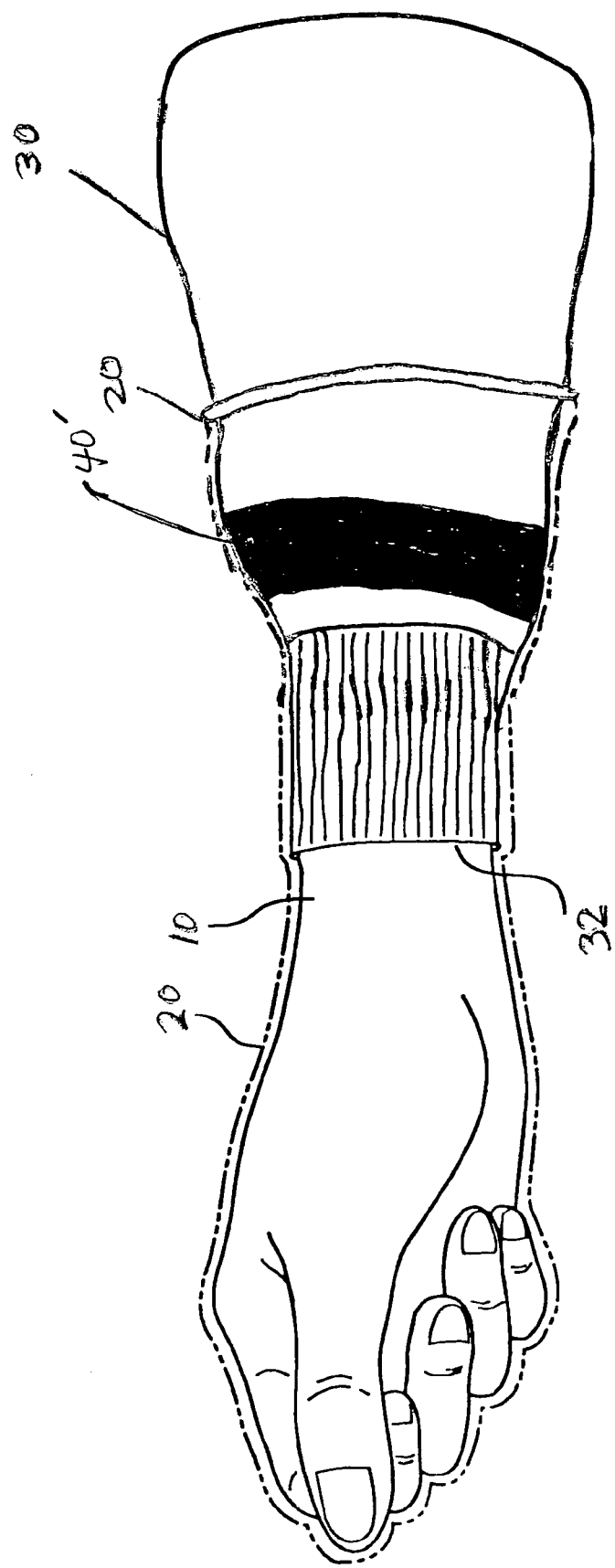
FIG. 4 illustrates a perspective view of an alternate embodiment of a nonwoven sleeve similar to FIG. 3, but having a single, relatively wide continuous ultrasonic bonded band positioned circumferentially about a sleeve surface.

In FIG. 4, a further alternate embodiment of the treated garment of FIG. 2 is illustrated. In this embodiment, a low surface tension liquid blocking material in the form of a single wide band 40' surrounds the garment sleeve 25. This region or band is also shown as visible through the glove 20, which is shown in phantom lines.

In FIGS. 5A–5C, several alternate embodiments of the treated garment are photographically illustrated. The garment 30 may include outwardly upturned end portions 42 of the edge 37 of the sleeve 25 and may also include, by way of non-limiting example, a leg edge, a neck edge and/or a waist edge that have been hemmed ultrasonically (not shown). Such upturned portions provide yet another structural barrier to the spread of wicking low surface tension liquid and other fluid. A cuff, of the type previously described herein could then be attached to the sleeve 25 at the hemmed area or sleeve edge 37 (FIG. 2). In FIG. 5A, a single low surface tension liquid blocking material 38 in the form of a patterned band 44 surrounds an upturned garment sleeve 25. The patterned band 44 provides both a low surface tension liquid blocking material 38 as well as a bond between the layers of the garment 30, if any. This band or pattern 44 provides both a gutter 46 and a holding area or pocket 48 (shown in FIG. 6) for retaining low surface tension liquid. In FIG. 5B, an alternative embodiment similar to that shown in 5A is illustrated, except that the patterned band 44 has a different pattern. In FIG. 5C, an alternative embodiment of the treated garment 30 is illustrated. In this embodiment, a pair of low surface tension liquid blocking materials 38 are provided in the form of a pair of patterned bands 44 which surround an upturned garment sleeve 25. The pair of bands 44 provide both low surface tension liquid blocking materials 38 as well as a pair of bonds (shown generally in FIG. 6) between the layers of the garment 30. The bands 44 provide gutters 46 and pockets 48 (FIG. 6) for retaining low surface tension liquid to be contained on an outer surface 35 on either side of the bands 44.

Figure 6:
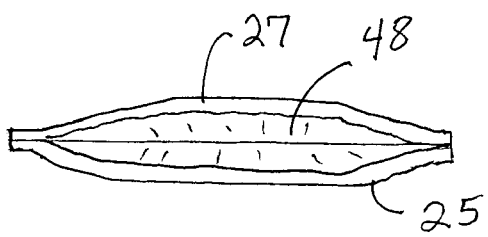
FIG. 6 is a sectional view of FIG. 5A taken along lines 6—6.

FIG. 6 is a sectional view of FIG. 5A taken along lines 6—6, illustrating a pocket 48 which is formed when one or more layers of the garment 30 is bonded to each other when thermally bonded or ultrasonically bonded to provide by one or more continuous bands, namely, but not by way of limitation, lines, paths, patterns, regions, and so forth of low surface tension liquid blocking materials, as is illustrated generally in FIGS. 5A–5C.

Figure 7:
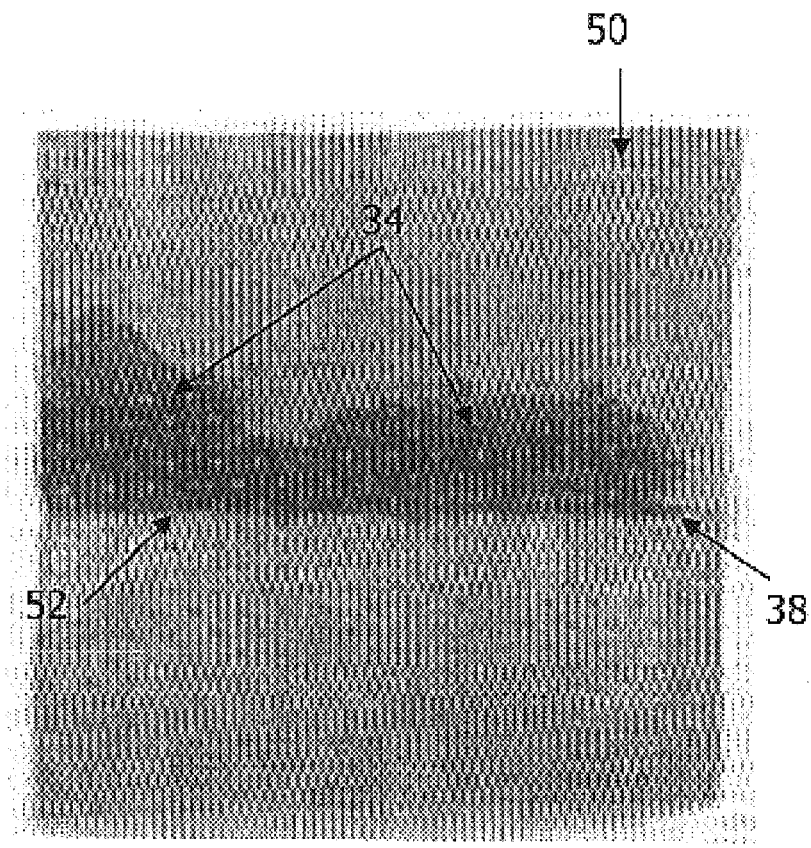
FIG. 7 is a photographic image thermal bonded nonwoven fabric in accordance with the present invention, showing the bond or weld inhibiting the wicking of fluid.

FIG. 7 is a photographic image of a nonwoven fabric 50 used in the present invention, showing the low surface tension liquid blocking material 38 formed by thermal bonding, provided in the form of a band or line 52 generally about ⅛ inch in width, which has substantially blocked wicking of a liquid 34 (which is a 20% isopropyl alcohol and water with red food coloring added to enhance visualization (the surface tension of the liquid being approximately 32 dynes/cm, as a preliminary model for blood having a surface tension of approximately 40 dynes/cm)) The use of thermal bonding will be discussed in greater detail below, in Example 1.

Such low surface tension liquid blocking materials are each desirably between about ⅛ to about 1 inch in width and are positioned in a continuous generally linear path around the circumference of the sleeve, leg, waist, or neck opening in a position around the circumference, equidistant from the garment opening. More desirably, such blocking materials have a width between about 3/16 and about ½ inch. If a low surface tension liquid blocking material is present either by itself, or in conjunction with additional blocking materials, it is desirable that such additional blocking materials have a width of between about ¼ and ½ inch in width. As previously indicated, it is desirable that such low surface tension liquid blocking materials not occupy the entire area of a limb, neck or abdominal portion of a garment, as such will have a negative impact on the comfort of a garment (limiting the ability of perspired moisture to leave the garment), such would appreciably add to the costs of a garment, and could negatively impact the ability of a glove or foot covering to stay situated over the garment as a result of low coefficients of friction (thereby leading to sliding of the glove along the garment during use). It therefore is desirable for an area of separation between regions or bands of blocking materials of between about ½ and 2 inches in width in order to maintain a high coefficient of friction between gloves or shoe coverings and gowns. More desirably, there is an area of separation between regions or bands of blocking materials of about 1 in width.

For the purposes of this application, the term "continuous region" shall be used to describe an area of the workwear having a low surface tension liquid blocking material having at least ⅛ inch width. For the purposes of this application the terms "line(s)", "path(s)", "band(s)" and/or "pattern(s)", shall refer to a continuous region around the garment sleeve, leg or opening, that is less than 1 inch width. Desirably, a band is present on a sleeve of a gown approximately between about ½ inch and about 6 inches from the edge of the gown cuff or sleeve edge surrounding the wrist of the user.

While numerous application methods may be used to provide low surface tension liquid blocking materials which significantly reduce or block low surface tension liquid, desirably, ultrasonic bonding or thermal bonding is used to apply a continuous band, region, pattern, and so forth to the protective workwear sleeve, leg, neck, abdominal, torso, and so forth areas of a garment or workwear.

Vibrational ultrasonic sewing machines are commercially available, and one such ultrasonic sewing machine, Model LM 1220 manufactured by Sonobond Ultrasonics, West Chester, Pa., was used to create the low surface tension liquid blocking materials illustrated in FIGS. 2 and 5A–5C. The useful range of frequencies is very wide. Frequencies of up to about 40 kHz and about 20 kHZ are often used commercially. However, frequencies of, for example, 18 kHz and as low as 10 kHz have also been used in some applications. The power settings used commercially are often in a range of 10 Watts to 1000 Watts, although other power settings may be utilized. Desirably, the power settings are in a range of about 50 Watts to about 900 Watts; more desirably, the power settings are in a range of about 100 Watts to about 500 Watts.

Desirably, the pressure settings for both the ultrasonic horn and the pattern wheel are set in a range of about 1 psi to about 100 psi. More desirably, the pressure settings for both the ultrasonic horn and the pattern wheel are in a range of about 5 psi to about 50 psi. More desirably, the pressure settings for both the ultrasonic horn and the pattern wheel are in a range of about 10 psi to about 40 psi.

The particular "pattern" used for the pattern wheel determines the width and pattern for the low surface tension liquid blocking material. Height and spacing of projections on the pattern wheel will be selected in accordance with the desired end product. For example, the height will preferably be approximately the thickness of the formed web of the garment, and the projections and/or pattern will preferably be continuous and sufficient to provide substantial lamination of the formed web, through all layers thereof.

The ultrasonic horn and the pattern wheel are each adjustable for varying speeds. Desirably, the horn and wheel are both set speeds in a range of about 1 foot per minute to about 100 feet per minute. More desirably, the horn and wheel are set at a speed of about 2 to about 60 feet per minute. Even more desirably, the horn and wheel are set at speeds of about 6 to about 40 feet per minute. When two similar materials are positioned in the nip between the ultrasonic horn and the pattern wheel, it is desirable to have the same speeds for both. When two different materials are positioned in the nip, for example, a textured material adjacent the ultrasonic horn and a non-textured material adjacent the pattern wheel, the speed of the wheel may need to be somewhat faster than the speed of the ultrasonic horn, due to the frictional differences between the textured and non-textured materials.

Heat or thermal sealing, and bonding of materials is well known in the art, and various thermal bonding equipment is discussed herein. One such piece of equipment utilized with the present invention is Vertrod Thermal Impulse Heat Sealer, available from Therm-O-Seal, Mansfield, Tex. The useful range of heat settings and speeds are very wide. However, heat settings creating a degree of melting of a nonwoven material without interfering with the integrity and continuity of the material, i.e., causing thinning, slitting or perforations, are generally accepted as optimal, and are commercially used. Such heat settings are desirably between about 150 degrees F. to about 400 degrees F. (about 66 degrees C. to about 205 degrees C.) More desirably, the heat settings are about 280 degrees F. to about 320 degrees F. (about 138 degrees C. to about 160 degrees C.). Speed settings for heat sealing or bonding nonwoven materials are desirably in a range of 1 foot per minute to about 60 feet per minute, although thermal sealing may be accomplished by hand at lower and/or varying speeds. It will be appreciated that the heat settings used will be adapted to the particular characteristics of the material; the speed used will be adapted to the length, curves, and so forth of the material as well. As noted previously herein, rollers and so forth may provide a linear seam or bond; continuous pattern(s) may be provided as well. As discussed above with reference to FIG. 5B, the continuous pattern may be supplemented with a discontinuous pattern, if desired.

As previously discussed herein, such ultrasonic bonding or thermal bonding as a treatment for limiting wicking of low surface tension liquid may be utilized with a variety of nonwoven fabrics. Desirably, such treatments are used on nonwoven materials such as those described in U.S. Pat. Nos. 4,535,481, 5,213,881, 5,271,883, 5,464,688, 5,695,868, 5,855,999, 6,037,281, each of which are hereby incorporated by reference in their entirety. Such materials include fibrous laminate materials such as spunbond-meltblown-spunbond fibrous materials and film-fiber laminate materials. Typically such materials have been produced by known nonwoven manufacturing processes that include bonding of the layers, such as thermal point bonding.

Figure 8:
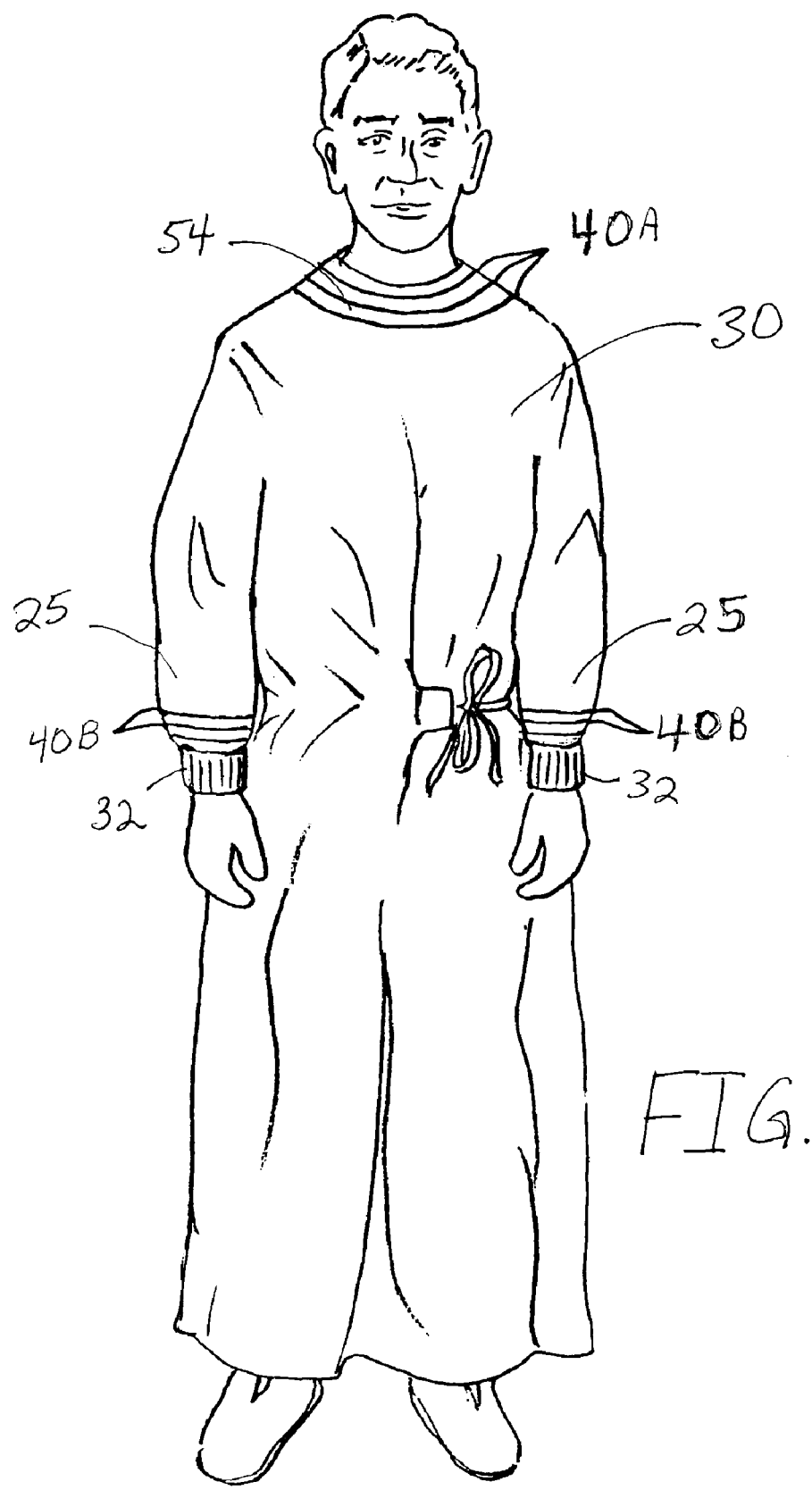
FIG. 8 illustrates an exemplary protective garment in accordance with the invention, namely a surgeon's gown.
Figure 9:
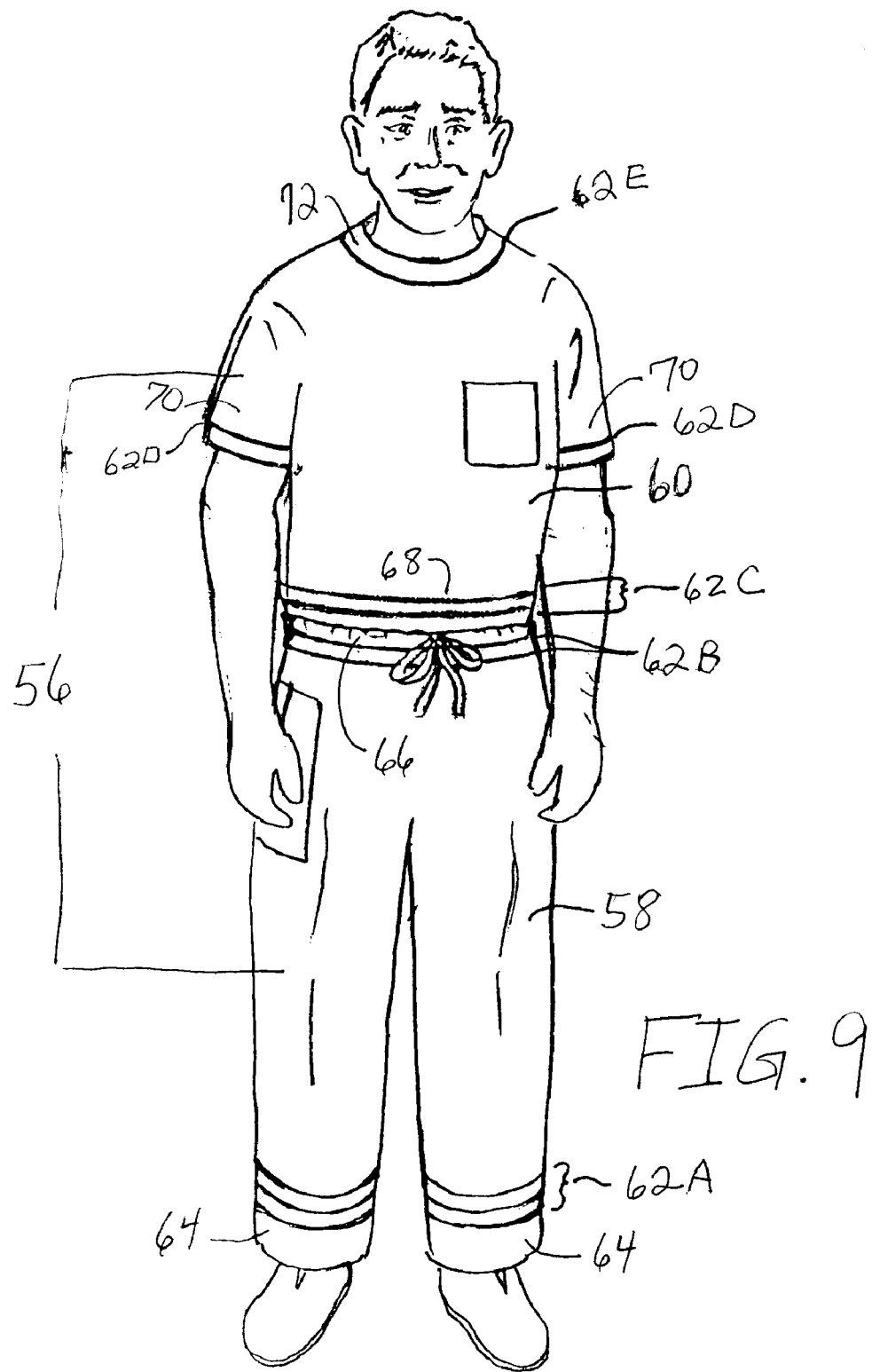
FIG. 9 illustrates another exemplary protective garment in accordance with the invention, names medical scrubs.

As illustrated in FIGS. 8 and 9, a wide variety of protective workwear may be treated with low surface tension liquid blocking material as previously described. For the purposes of example only, as can be seen in FIG. 8, a surgical gown or garment 30 which has been treated with such blocking material to provide a plurality of bands 40A at the neck 54 and a plurality of bands 40B at the sleeve 25. As can be seen in FIG. 9, a medical scrub set 56, consisting of a pant garment 58 and a shirt garment 60, has single or a plurality of bands 62A of low surface tension liquid blocking material on the leg/ankle areas 64, waist area 66 (bands 62B), shirt tail area 68 (bands 62C) arm areas 70 (bands 62D), and neck area 72 (band 62E). In an alternate embodiment, the cuff, neck opening, or waist opening of such a garment may be further treated to include hydrophobic or other repellant coatings. Such repellant coatings include fluorochemical coatings such as those described in U.S. Pat. Nos. 5,151,321, 5,116,682, and 5,145,727, all of which are incorporated in their entirety by reference herein. Additional treatment is described in detail below, in Example 2.

The present invention is desirably used with an improved cloth-like, liquid-impervious, breathable barrier material, such as that disclosed in U.S. Pat. No. 6,037,281, which is incorporated in its entirety herein, and which is discussed below in detail herein. The breathable barrier material possesses a unique balance of performance characteristics and features making the material suitable for use in forming surgical articles, as well as other garment and over-garment applications, such as personal protective equipment applications. The barrier material is a laminate comprising three layers—a top nonwoven layer formed, for example, of spunbond filaments, a bottom nonwoven layer formed, for example, of spunbond filaments, and a middle breathable film layer formed, for example, of a microporous film. The individual layers of barrier material are laminated, bonded or attached together by known means, including thermal-mechanical bonding, ultrasonic bonding, adhesives, and the like. As used herein, the terms "layer" or "web" when used in the singular can have the dual meaning of a single element or a plurality of elements.

Commercially available thermoplastic polymeric materials can be advantageously employed in making the fibers or filaments from which the top and bottom layers are formed. As used herein, the term "polymer" shall include, but is not limited to, homopolymer, copolymers, such as, for example, block, graft, random and alternating copolymers, terpolymers, etc., and blends and modifications thereof. Moreover, unless otherwise specifically limited, the term "polymer" shall include all possible geometric configurations of the material, including, without limitation, isotactic, syndiotactic, random and atactic symmetries. As used herein, the terms "thermoplastic polymer" or "thermoplastic polymeric material" refer to a long-chain polymer that softens when exposed to heat and returns to the solid state when cooled to ambient temperature. Exemplary thermoplastic materials include, without limitation, polyvinyl chlorides, polyesters, polyamides, polyfluorocarbons, polyolefins, polyurethanes, polystyrenes, polyvinyl alcohols, caprolactams, and copolymers of the foregoing.

Nonwoven webs that can be employed as the nonwoven top and bottom layers can be formed by a variety of known forming processes, including spunbonding, airlaying, meltblowing, or bonded carded web formation processes. For example, the top layer and bottom layer are both spunbond nonwoven webs, which have been found advantageous in forming barrier material. Spunbond nonwoven webs are made from melt-spun filaments. The melt-spun filaments are deposited in a substantially random manner onto a moving carrier belt or the like to form a web of substantially continuous and randomly arranged, melt-spun filaments. Spunbond filaments generally are not tacky when they are deposited onto the collecting surface. The melt-spun filaments formed by the spunbond process are generally continuous and have average diameters larger than 7 microns based upon at least 5 measurements, and more particularly, between about 10 and 100 microns. Another frequently used expression of fiber or filament diameter is denier, which is defined as grams per 9000 meters of a fiber or filament.

Spunbond webs generally are stabilized or consolidated (pre-bonded) in some manner immediately as they are produced in order to give the web sufficient integrity and strength to withstand the rigors of further processing. This pre-bonding step may be accomplished through the use of an adhesive applied to the filaments as a liquid or powder which may be heat activated, or more commonly, by an air knife or compaction rolls. As used herein, the term "compaction rolls" means a set of rollers above and below the nonwoven web used to compact the web as a way of treating a just produced, melt-spun filament, particularly spunbond, web, in order to give the web sufficient integrity for further processing, but not the relatively strong bonding of later applied, secondary bonding processes, such as through-air bonding, thermal bonding, ultrasonic bonding and the like. Compaction rolls slightly squeeze the web in order to increase its self-adherence and thereby its integrity. An air knife, as its name implies, directs heated air through a slot or row of openings onto the web to compact and provide initial bonding.

An exemplary secondary bonding process utilizes a patterned roller arrangement for thermally bonding the spunbond web. The roller arrangement typically includes a patterned bonding roll and a smooth anvil roll which together define a thermal patterning bonding nip. Alternatively, the anvil roll may also bear a bonding pattern on its outer surface. The pattern roll is heated to a suitable bonding temperature by conventional heating means and is rotated by conventional drive means, so that when the spunbond web passes through the nip, a series of thermal pattern bonds is formed. Nip pressure within the nip should be sufficient to achieve the desired degree of bonding of the web, given the line speed, bonding temperature and materials forming the web. Percent bond areas within the range of from about 10 percent to about 20 percent are typical for such spunbond webs.

The middle breathable film layer can be formed of any microporous film that can be suitably bonded or attached to top and bottom layers to yield a barrier material having the unique combination of performance characteristics and features described herein. A suitable class of film materials includes at least two basic components: a thermoplastic elastomeric polyolefin polymer and a filler. These (and other) components can be mixed together, heated and then extruded into a mono-layer or multi-layer film using any one of a variety of film-producing processes known to those of ordinary skill in the film processing art. Such film-making processes include, for example, cast embossed, chill and flat cast, and blown film processes.

Generally, on a dry weight basis, based on the total weight of the film, the middle breathable film layer will include from about 30 to about 60 weight percent of the thermoplastic polyolefin polymer, or blend thereof, and from about 40 to about 70 percent filler. Other additives and ingredients may be added to the film layer 14 provided they do not significantly interfere with the ability of the film layer to function in accordance with the teachings of the present invention. Such additives and ingredients can include, for example, antioxidants, stabilizers, and pigments.

In addition to the polyolefin polymer, the middle breathable film layer also includes a filler. As used herein, a "filler" is meant to include particulates and other forms of materials which can be added to the film polymer extrusion blend and which will not chemically interfere with the extruded film but which are able to be uniformly dispersed throughout the film. Generally, the fillers will be in particulate form and may have a spherical or non-spherical shape with average particle sizes in the range of about 0.1 to about 7 microns. Both organic and inorganic fillers are contemplated to be within the scope of the present invention provided that they do not interfere with the film formation process, or the ability of the film layer to function in accordance with the teachings of the present invention. Examples of suitable fillers include calcium carbonate ($CaCO_3$), various kinds of clay, silica ($SiO_2$), alumina, barium carbonate, sodium carbonate, magnesium carbonate, talc, barium sulfate, magnesium sulfate, aluminum sulfate, titanium dioxide ($TiO_2$), zeolites, cellulose-type powders, kaolin, mica, carbon, calcium oxide, magnesium oxide, aluminum hydroxide, pulp powder, wood powder, cellulose derivatives, chitin and chitin derivatives. A suitable coating, such as, for example, stearic acid, may also be applied to the filler particles.

As mentioned herein, the breathable film layer may be formed using any one of the conventional processes known to those familiar with film formation. The polyolefin polymer and filler are mixed in appropriate proportions given the ranges outlined herein and then heated and extruded into a film. In order to provide uniform breathability as reflected by the water vapor transmission rate of the film, the filler should be uniformly dispersed through-out the polymer blend and, consequently, throughout the film layer itself so that upon stretching pores are created to provide breathability. For purposes of the present invention, a film is considered "breathable" if it has a water vapor transmission rate of at least 300 grams per square meter per 24 hours (g/m2/24 hours), as calculated using the test method described herein. Generally, once the film is formed, it will have a weight per unit area of less than about 80 grams per square meter (gsm) and after stretching and thinning, its weight per unit area will be from about 10 gsm to about 25 gsm.

The breathable film layer used in the example of the present invention described below is a mono-layer film, however, other types, such as multi-layer films, are also considered to be within the scope of the present invention provided the forming technique is compatible with filled films. The film as initially formed generally is thicker and noisier than desired, as it tends to make a "rattling" sound when shaken. Moreover, the film does not have a sufficient degree of breathability as measured by its water vapor transmission rate. Consequently, the film is heated to a temperature equal to or less than about 5 degrees C. below the melting point of the polyolefin polymer and then stretched using an in-line machine direction orientation (MDO) unit to at least about two times (2×) its original length to thin the film and render it porous. Further stretching of the middle breathable film layer, to about three times (3×), four times (4×), or more, its original length is expressly contemplated in connection with forming middle breathable film layer. After being stretch-thinned, the middle breathable film layer should have an "effective" film gauge or thickness of from about 0.2 mil to about 0.6 mil. The effective gauge is used to take into consideration the voids or air spaces in breathable film layers.

Cuffs 32, as photographically illustrated in FIGS. 1, 2, 10A and 10B, are also desirably used in the present workwear or medical garments 30, and such cuffs 32 are attached to the wrist end or sleeve edge 37 of each sleeve 25. Cuffs may also be attached to the garment at the end of each pant leg, the neck of each garment, or as a waist band of shirt and/or pants, and so forth (not shown). Such cuffs are desirably made from elastic yarns formed from synthetic or natural materials. An example of a synthetic material for forming the elastic yarns is polyurethane. Spandex is an example of polyurethane-based elastomer. More particularly, spandex is a polyurethane in fiber form containing a thermoplastic polyurethane elastomer with at least 85% polyurethane content. Commercial examples of spandex include LYCRA, VYRENE, DORLASTAN, SPANZELLE and GLOSPAN. An example of a natural material for forming elastic yarns is natural rubber. Polyester, nylon, and combinations of any of the foregoing synthetic and/or natural elastic yarns may also be used. The use of these, and other materials to construct sleeves and/or cuffs is disclosed in U.S. Pat. No. 5,594,955, which is incorporated by reference in its entirety herein.

In the present embodiment, cuffs 32 are desirably sewn, thermally bonded, ultrasonically bonded, adhesively attached, and so forth to the lower end or sleeve edge 37 of the sleeve 25. Desirably, the cuffs 32 are sewn onto the sleeve 25 using a thread or yarn treated to be substantially repellant to low surface tension liquids. Desirably, the cuffs 32 are also treated to be substantially repellant to low surface tension liquids as well.

Figure 10A:
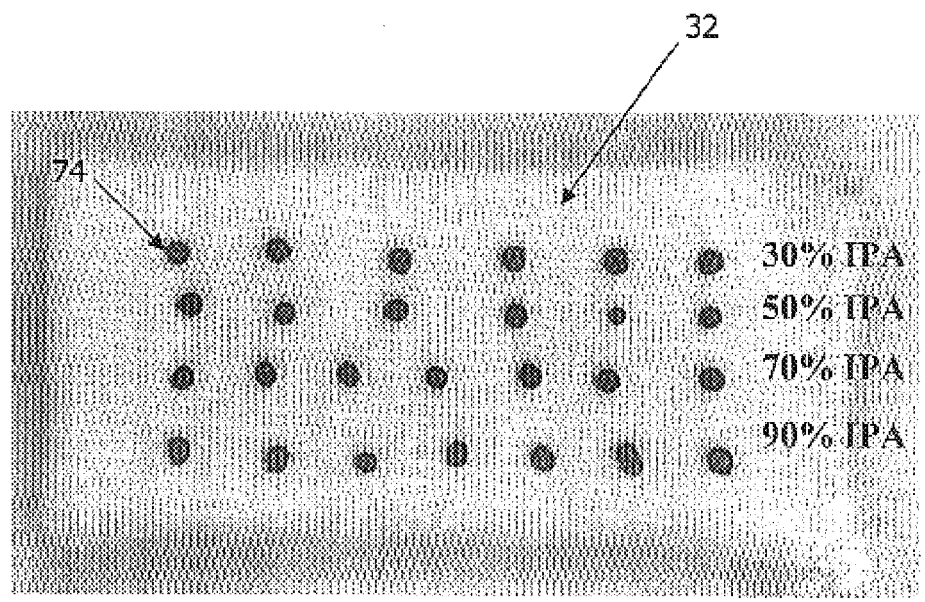
FIGS. 10A–10B are photographic images of a cuff treated to repel low surface tension liquids with the liquid beaded on the surface (10A) and with the cuff of FIG. 10A dried with a towel, showing substantial repelling/blocking of low surface tension liquids (10B).
Figure 10B:
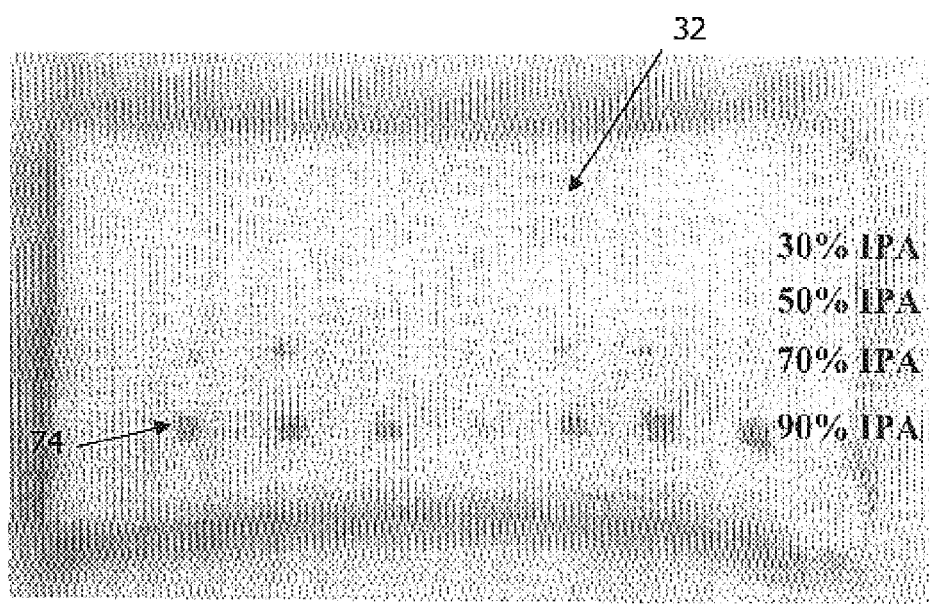

FIGS. 10A and 10B provide photographic images of treated cuffs. FIG. 10A shows a polyester cuff 32 which treated to repel low surface tension liquids. The cuff 32 was treated by first preparing a fluorochemical emulsion, described below in Example 2. The treated cuff 32 then received "drops" of a liquid (only one "drop" of the plurality of liquid drops designated by the numeral 74); Each row of liquid drops 74 labeled 30% IPA, 50% IPA, 70% IPA and 90% IPA (drops of liquid were in separate lines of 30%, 50%, 70%, and 90% isopropyl alcohol and water with red food coloring for ease of visualization to compare to blood which has a surface tension of approximately 40 dynes/cm). All liquid drops applied in each row in drop form are at least somewhat beaded on the surface.

FIG. 10B shows the same polyester cuff 32 of FIG. 10A, but dried with a towel, to display that a significant plurality of the drops of low surface tension liquids were blocked/repelled. The treated cuffs 32, dried with a towel, as illustrated in FIG. 10B, substantially repelled the 30% IPA and 50% IPA liquid, partially repelled the 70% IPA liquid, and slightly repelled the 90% IPA liquid. Any "cuff" may be used on or around any portion(s) of the medical garment. It will be appreciated that such treatment may be provided for any portion and/or all of the workwear, the cuffs, or both. Such treatment of a cuff is described in further detail in Example 2, below.

Although various embodiments of garment configurations have been described above, it should be understood, that workwear of the present invention may generally have any configuration desired, and need not contain all of the components described above. The present invention may be better understood with reference to the following examples, which are not meant to be limiting.

EXAMPLES

Example 1

Three sets of 8 inch by 10 inch sheets were cut from a roll of fabric (MICROCOOL®, available from Kimberly-Clark Corporation, Roswell, Ga., using a hydraulic press. The fabric, described above in detail and in U.S. Pat. No. 6,037,281 (previously incorporated by reference herein in its entirety), is a three layer laminate made generally from a layer of spunbond material (SB), a breathable film, and an SMS laminate. The body side or inside surface of the fabric is a 0.75 osy SMS, the exterior or outer surface is a 0.6 osy SB material, and the middle layer of the laminate is a cast film consisting of polypropylene skins and a linear low density polyethylene (LLDPE) core filled with $CaCO_3$ and stretched to generate micropores for breathability.

Three sheets were utilized and were treated to provide a single thermal bond in the form of a line across each sheet; each line was each approximately one eighth inch in width. Each thermal bond line was produced using Vertrand Thermal Impulse Heat Sealer, available from Therm-O-Seal, Mansfield, Tex. Heat Settings of 1.0, 1.25, and 1.5, respectively, were used (thermal settings believed to be about 250 degrees F. to about 350 degrees F. (121 degrees C. to about 177 degrees C.). The sheets were each hand-directed through the thermal/heat sealer. The pressure applied was about 30 psi.

The width of the thermal bond, the amount of heat applied, and the speed at which it is required to provide adequate anti-wicking properties will depend on the actual non-woven materials to be treated and the low surface tension liquid to be blocked. The treatment pattern can be any pattern, but is desirably a continuous pattern such as a solid line which completely encircles/circumscribes the garment surrounding the covered limb or anatomical region (neck, torso).

In the first example, each sheet was positioned on a horizontal surface. Three milliliters of a low surface tension liquid (32 dynes/cm) comprising 20% isopropyl alcohol and water colored with red food coloring (to allow for clear visualization), was placed by burette in drops one inch above the treated area. Each sheet was then moved to a surface with a 45 degree incline, with the treated area at the highest incline. At a line thickness of about one eighth inch, it was noted that wicking of liquid in all three samples was substantially blocked, as is generally photographically illustrated by one of the samples, shown in FIG. 7.

As can be seen in FIG. 7, a nonwoven material treated by thermal bonding a line of approximately one eighth inch is shown. It can be seen that the thermal bond substantially blocks the wicking of liquids along the fibers of the nonwoven material.

Example 2

A polyester cuff was provided, as shown in the photographic images of FIGS. 10A and 10B. FIG. 10A shows a cuff 32 which has been treated to repel or block low surface tension liquids. The treated cuff 32 was treated by first preparing a fluoro-chemical emulsion of 2% weight TG-KC01, available from Daikin America, Decatur, Alabama, 0.25% 1-Octanol available from Sigma-Aldrich, St. Louis, Mo., and 97.75% deionized water. The cuff 32 was dipped into the emulsion until saturated, then passed through a nip (100 psi) to squeeze off the excess formulation. The damp cuff was dried in a convection oven at 105 degrees C. for 10 minutes to evaporate the remaining water and to cure the fluorochemical. After receiving the treatment, drops 74 of a liquid in lines labeled 30% IPA, 50% IPA, 70% IPA and 90% by volume IPA (corresponding directly to a liquid solution of 30%, 50%, 70% and 90% by volume isopropyl alcohol and water with red food coloring for ease of visualization formulation; the 50% IPA mixture having a surface tension of about 28 dynes/cm) were applied in rows, as illustrated in FIG. 10A. All drops of the liquid in each line appeared to bead on the surface of the cuff 32.

FIG. 10B shows the treated polyester cuff 32 of FIG. 10A, which has been dried with a towel after application of the rows of drops 74 of low surface tension liquid. The cuff 32 substantially blocked/repelled the 30% IPA and 50% IPA liquid, partially repelled/blocked the 70% IPA liquid, and somewhat repelled/blocked the 90% IPA liquid.

Example 3

A commercial medical garment having a sleeve 25 (without low surface tension liquid blocking material) was provided, as shown generally in FIG. 1, which had an untreated polyester cuff 32' (illustrated generally in FIG. 10A) sewn to the wrist end of the sleeve 25. The sleeve 25 with cuff 32 were positioned over a porcelain model of a medical service provider's hand 10. A surgical glove 20 was positioned over the sleeve 25, and pulled up three (3) inches past the cuff. The hand 10 of the porcelain model was positioned downward at a forty-five (45) degree incline to simulate a medical service provider's general hand position. A low surface tension liquid 34 (isopropyl alcohol and water colored with red food coloring, for enhanced visualization (having a surface tension of approximately 32 dynes/cm)) was provided. Ten (10) milliliters of the liquid 34 was disposed dropwise on the sleeve 25 one (1) inch above the top of the glove 20.

As shown in FIG. 1, the commercial sleeve 25 allowed the low surface tension liquid 34 to wick down to the cuff 32. After removing the sleeve 25 from the mold hand 10, it was apparent that the liquid 34 had wicked onto the hand and up the inner surface of the sleeve 25, contacting the arm of the mold as well.

Another sleeve 25 was provided in accordance with the present invention, as shown in FIG. 2. A sheet having dimensions of twelve (12) inches by ten (10) inches was cut from a roll of fabric (MICROCOOL®, available from Kimberly-Clark Corporation, Roswell, Ga. One of the twelve (12) inch edges was then turned upward and folded back approximately one (1) inch and ultrasonically bonded to provide a continuous band of low surface tension liquid blocking material 38, thereby also providing a gutter and a pocket (similar to the sleeve shown in FIG. 5B). The bonding was accomplished by using an a Model LM 1220 Sonobond Lacemaster/Seammaster Ultrasonic Sewing Machine available from Sonobond Ultrasonics, West Chester Pa. The ultrasonic sewing machine had a frequency setting of 20 kHz, a pressure setting of 2 (30 psi), a power setting of 4 (about 400 Watts), and the speed of both the anvil and the pattern horn was set at 1.2 (about 7 ft/min.).

The ten (10) inch edges were then overlapped and ultrasonically hemmed or bonded together, to form a mock MICROCOOL® garment sleeve 25. A treated cuff 32, which was treated as described in detail above in Example 2, and illustrated in FIG. 10B, was attached to the wrist end (sleeve edge) of the sleeve 25 via a fabric tape (not shown). A surgical glove 20 was positioned over the sleeve 25, and pulled up approximately two (2) inches above the upturned hem of the sleeve 25, approximately three (3) inches above the cuff 32. The hand 10 of the porcelain model was positioned downward at a forty-five (45) degree incline to simulate a medical service provider's general hand position. A low surface tension liquid 34 (isopropyl alcohol and water colored with red food coloring, for enhanced visualization (having a surface tension of approximately 32 dynes/cm)) was again provided. Ten (10) milliliters of the liquid 34 was disposed dropwise on the sleeve 25 one (1) inch above the top of the glove 20.

As shown in FIG. 2, a discrete line of blocking material 38 is evident on the sleeve 25 which separates a portion of the sleeve 25 that has been exposed to a low surface tension liquid 34, and a portion of the sleeve 25 which has not. After removing the sleeve 25 from the mold hand 10, it was apparent that the low surface tension liquid 34 wicked into the pocket and along the gutter created by low surface tension blocking material 38. An amount of the low surface tension liquid had wicked across the inner glove surface to the cuff 32. The cuff 32 showed no signs, however, of the liquid 34. The sleeve 25, by way of the blocking material 38, the pocket (not shown), and the cuff 32 prevented the low surface tension liquid 34 from wicking onto the hand 10 Further, no liquid was found to have wicked into the interior of the sleeve, or on the arm; both the hand 10 and the arm were dry. Therefore, the low surface tension liquid 34 is maintained on the outer surface 35 of the sleeve 25.

While the present invention has been described in connection with certain desired embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. Protective workwear for covering a body portion, said protective workwear having an inner surface and an outer surface, at least said outer surface including thereupon a low surface tension liquid blocking material in a continuous unbroken band for blocking the wicking of at least low surface tension liquid that is contained on the outer surface of said outerwear, the blocking material formed by bonding at least a portion of the outer surface of the protective workwear in at least one continuous unbroken band, said bonding configured to melt, block and seal pores in a bonded area which form the band such that wicking of low surface tension liquid beyond the band is prevented, wherein no additional material is added to the protective workwear to provide the band.

2. The protective workwear of claim 1, wherein said low surface tension liquid blocking material is present on at least the outer surface in a plurality of bands.

3. The protective workwear of claim 1, wherein said low surface tension liquid blocking material is provided by thermally bonding at least a portion of the outer surface of the workwear to provide at least one band.

4. The protective workwear of claim 1, wherein said low surface tension liquid blocking material is provided by ultrasonically bonding at least a portion of the outer surface of the workwear to provide at least one band.

5. The protective workwear of claim 1, wherein when one portion of the workwear is overlapped on another portion and bonded together, it provides the low surface tension liquid blocking material.

6. The protective workwear of claim 1, wherein said protective workwear is a medical garment.

7. The protective workwear of claim 6, wherein said medical garment is selected from the group consisting of hospital gowns, surgical gowns, medical scrubs, and medical drapes.

8. A protective workwear garment having an inner surface and an outer surface comprising:
    a body portion;
    a neck portion;
    two sleeves attached to the body portion, each sleeve having an inner surface and an outer surface, each sleeve comprising a lower edge for encircling a user's wrist, an elbow region for containing a user's elbow, and an upper edge attached to said body portion, wherein said sleeves include along at least their outer surfaces a low surface tension liquid blocking material in a continuous unbroken band for blocking the wicking of at least low surface tension liquid that is contained on said outer surface of said outerwear, the blocking material formed by bonding at least a portion of the outer surface of the sleeve in at least one continuous unbroken band, said bonding configured to melt, block and seal pores in a bonded area which forms the band such that wicking of low surface tension liquid beyond the band is prevented, wherein no additional material is added to the protective workwear to provide the band.

9. The protective workwear garment of claim 8, wherein low surface tension liquid blocking material is located on said sleeves between the sleeve lower edge and the elbow region.

10. The protective workwear garment of claim 8, wherein low surface tension liquid blocking material is located adjacent the neck portion along the garment outer surface.

11. The protective workwear garment of claim 8, wherein said low surface tension liquid blocking material is provided by thermally bonding at least a portion of the outer surface of the workwear to provide at least one band.

12. The protective workwear garment of claim 8, wherein said low surface tension liquid blocking material is provided by ultrasonically bonding at least a portion of the outer surface of the workwear to provide at least one band.

13. The protective workwear garment of claim 8, wherein when one portion of the workwear is overlapped on another portion and bonded together, it provides the low surface tension liquid blocking material.

14. The protective workwear garment of claim 8, wherein said low surface tension liquid blocking material is present on said outer surface of said sleeves in a plurality of bands.

15. The protective workwear garment of claim 8, wherein said protective workwear is a medical garment.

16. The protective workwear garment of claim 15, wherein said medical garment is selected from the group consisting of hospital gowns, surgical gowns, and medical scrubs.

17. A protective workwear garment having an inner surface and an outer surface comprising:
    a body portion;
    a neck portion;
    two sleeves attached to the body portion, each sleeve having an inner surface and an outer surface, each sleeve comprising a lower edge for encircling a user's wrist, an elbow region for containing a user's elbow, and an upper edge attached to said body portion, cuffs attached to the lower edge of each sleeve, the cuffs treated to block wicking of fluids, wherein said sleeves include along at least their outer surfaces a low surface tension liquid blocking material in a continuous unbroken band for blocking the wicking of at least low surface tension liquid that is contained on said outer surface of said outerwear, the blocking material formed by bonding at least a portion of the outer surface of the sleeve in at least one continuous unbroken band, said bonding configured to melt, block and seal pores in a bonded area which forms the band such that wicking of low surface tension liquid beyond the band is prevented, wherein no additional material is added to the protective workwear to provide the band.

18. The protective workwear garment of claim 17, wherein said low surface tension liquid blocking material is provided by thermally bonding at least a portion of the outer surface of the workwear to provide at least one band.

19. The protective workwear garment of claim 17, wherein said low surface tension liquid blocking material is provided by ultrasonically bonding at least a portion of the outer surface of the workwear to provide at least one band.

20. The protective workwear garment of claim 17, wherein when one portion of the workwear is overlapped on another portion and bonded together, it provides the low surface tension liquid blocking material.

21. The protective workwear garment of claim 17, wherein said low surface tension liquid blocking material is present on said outer surface of said sleeves in a plurality of bands.

22. The protective workwear garment of claim 17, wherein said protective workwear garment is a medical garment.

23. The protective workwear garment of claim 22, wherein said medical garment is selected from the group consisting of hospital gowns, surgical gowns, and medical scrubs.

* * * * *